United States Patent
Rasmussen et al.

(10) Patent No.: US 8,709,064 B2
(45) Date of Patent: Apr. 29, 2014

(54) INTRODUCER ASSEMBLY AND DILATOR TIP THEREFOR

(75) Inventors: Erik E. Rasmussen, Slagelse (DK); Bent Oehlenschlaeger, Ll. Skensved (DK)

(73) Assignee: Cook Medical Technologies LLC, Bloomington, IN (US)

( * ) Notice: Subject to any disclaimer, the term of this patent is extended or adjusted under 35 U.S.C. 154(b) by 77 days.

(21) Appl. No.: 13/294,651

(22) Filed: Nov. 11, 2011

(65) Prior Publication Data

US 2012/0123464 A1 May 17, 2012

(30) Foreign Application Priority Data

Nov. 12, 2010 (GB) .................................. 1019107.0

(51) Int. Cl.
*A61F 2/06* (2013.01)
(52) U.S. Cl.
USPC ....................................................... 623/1.13
(58) Field of Classification Search
USPC ........ 606/108, 191, 194, 198; 623/1.11, 1.12, 623/1.13, 1.23, 2.11
See application file for complete search history.

(56) References Cited

U.S. PATENT DOCUMENTS

| | | | |
|---|---|---|---|
| 6,514,228 B1 | 2/2003 | Hamilton et al. | |
| 7,147,657 B2 * | 12/2006 | Chiang et al. ................. | 623/1.11 |
| 7,618,431 B2 | 11/2009 | Roehm, III et al. | |
| 7,911,529 B2 * | 3/2011 | Ehara et al. .................... | 348/362 |
| 2004/0116899 A1 | 6/2004 | Shaughnessy et al. | |
| 2005/0149096 A1 | 7/2005 | Hilal et al. | |
| 2007/0219466 A1 | 9/2007 | Tremulis et al. | |
| 2008/0009929 A1 * | 1/2008 | Harris et al. ................... | 607/116 |

FOREIGN PATENT DOCUMENTS

| | | |
|---|---|---|
| EP | 1647233 A1 | 4/2006 |
| WO | 0051674 A1 | 9/2000 |
| WO | 2005/023359 A1 | 3/2005 |
| WO | 2010123663 A2 | 10/2010 |

OTHER PUBLICATIONS

Application No. 11275142.5-1526, EPO Search Report, Feb. 2, 2012, Cook Medical Technologies LLC.

* cited by examiner

*Primary Examiner* — Tuan V Nguyen
(74) *Attorney, Agent, or Firm* — Richard J. Godlewski

(57) ABSTRACT

An introducer assembly (60) is provided with a dilator tip (40) which has at least one portion (46) which is asymmetric in transverse cross-section, preferably being flattened or oval. A dilator tip (40) which is asymmetric over at least a part of its length gives the tip different flexure characteristics in different radial directions (54, 56). This provides advantages in trackability of the dilator tip (40) and thus of the introducer assembly (60) as well as providing for self-orientation of the dilator tip (40), useful in orienting medical devices or treatment tools.

13 Claims, 4 Drawing Sheets

INTRODUCER ASSEMBLY AND DILATOR TIP THEREFOR

TECHNICAL FIELD

The present invention relates to an introducer assembly and to a dilator tip therefor, in the preferred embodiment to a self-orienting dilator tip.

BACKGROUND ART

Introducers for deploying medical devices or for inserting treatment tools into the vasculature of a patient are well known in the art. Introducers for these applications are typically elongate tubular constructs which are fed through the vasculature of the patient up to the treatment site. An introducer needs to be flexible so as to be able to curve through the patient's vasculature. A flexible dilator tip is typically provided at the distal end of the introducer assembly, for use in guiding the introducer assembly to the treatment site. The guide wire may be provided for assisting in the insertion of the introducer assembly into the patient, the dilator tip and catheter elements of the assembly fitting over the guide wire.

Typically, the introducer assembly is generally round in axial cross-section in order to provide the assembly with similar being characteristics in all radial directions of the assembly. This applies equally to the dilator tip.

Problems can occur with the deployment of medical devices or tools using introducer assemblies, particularly in very tortuous paths, past aneurysms and also when seeking to orient a device or tool within a patient's vessel.

Some examples of introducer assemblies and dilator tips can be found in EP-1,647,233, U.S. Pat. No. 6,514,228, U.S. Pat. No. 7,618,431, and US-2005/149096.

DISCLOSURE OF THE INVENTION

The present invention seeks to provide an improved introducer assembly and an improved dilator tip for an introducer assembly.

According to an aspect of the present invention, there is provided an introducer assembly for the deployment of medical devices within a lumen of a patient, the assembly including a sheath member provided with at least one lumen therein for housing an implantable medical device or medical treatment apparatus; and a dilator tip extending beyond a distal extremity of the sheath member; the dilator tip including a proximal end, a distal end and a thickness in a direction substantially orthogonal to an axis between the proximal and distal ends; wherein the thickness of the dilator tip is for at least a portion of its extent between the proximal and distal ends non-round so as to have a lesser thickness in one angular direction relative to another.

Prior art dilator tips are generally round in axial cross-section, which gives them a similar flexibility in all radial directions. On the other hand, providing a dilator tip which is at least partially non-round in axial cross-section, or asymmetric, gives the dilator tip different flexibilities in different radial directions. This can, as explained below, improve the trackability of the dilator tip within a patient's vasculature and can also assist in the orientation of the distal end of the introducer assembly.

Preferably, the dilator tip is flattened for at least said portion. The term flattened as used herein denotes a shape in which along one radial direction the dilator tip is wider compared to its width in a radial direction 90 degrees offset from said one radial direction.

In the preferred embodiment, the dilator tip is oval in cross-section in said orthogonal direction for at least said portion.

The dilator tip typically tapers for at least a part thereof in a direction from its proximal end to its distal end.

Advantageously, said portion extends along substantially the entirety of the tapering part of the dilator tip.

In an embodiment, the dilator tip is varyingly non-round over at least said portion. The dilator tip may be increasingly flattened in a direction from its distal end to its proximal end. The increasing flattening is preferably gradual over at least said portion.

Having a shape which is increasingly flattened towards the distal end of the dilator tip gives this improved flexibility at its distal end and also, it has been found, contributes to improved trackability.

The dilator tip may include a proximal part which is not tapered in a direction towards the distal end of the dilator tip. In one embodiment, the proximal part is substantially round in axial cross-section. This shape is consistent with existing sheaths of round cross-section and thus enables the proximal end of the dilator tip to fit into the distal end of the sheath.

In another embodiment, the proximal part of the dilator tip is non-round in axial cross-section. For instance, the proximal part may be substantially flattened in axial cross-section. This gives the entirety of the dilator tip a non-rounded, preferably a flattened, cross-section and thus the entirety of the dilator tip has a non-uniform flexibility in different radial directions. This can maximise trackability and also self-orienting characteristics of the dilator tip. Furthermore, such a shape of dilator tip can be used with sheaths which are non-round (for instance oval) in internal cross-section.

Preferably, the dilator tip is formed from an elastomeric material, a plastics material, or a rubber or rubber like material. It may be formed from any of the materials commonly used in the art.

In a practical embodiment, the dilator tip includes a central lumen for the passage of a guide wire therethrough.

In the preferred embodiment, the non-round portion of the dilator tip provides the dilator tip with a radial orientation. Specifically, the dilator tip is preferably more flexible in one radial orientation relative to another as a result of the non-round portion.

Advantageously, the introducer assembly includes fixings for fixing an implantable medical device or other medical element in the introducer in a specific radial orientation, which radial orientation is aligned with the radial orientation of the dilator tip. Similarly, the introducer assembly may include an implantable medical device or other medical element having a given radial orientation profile, which profile is aligned with the radial orientation of the dilator tip.

Thus, the dilator tip can be used to orient a medical device carried on the introducer assembly, considerably facilitating the process of positioning and deployment of the device in a patient.

According to another aspect of the present invention, there is provided a dilator tip for an introducer assembly for the deployment of medical devices within a lumen of a patient, the dilator tip including a proximal end, a distal end and a thickness in a direction substantially orthogonal to an axis between the proximal and distal ends; wherein the thickness of the dilator tip is for at least a portion of its extent between the proximal and distal ends non-round so as to have a lesser thickness is one angular direction relative to another.

Preferably, the dilator tip is flattened for at least said portion.

Advantageously, the dilator tip tapers for at least a part thereof in a direction from its proximal end to its distal end.

According to another aspect of the present invention, there is provided an introducer assembly for the deployment of medical devices within a lumen of a patient, the assembly including a catheter portion provided with at least one lumen therein for holding an implantable medical device or medical treatment apparatus; and a dilator tip extending beyond a distal extremity of the catheter portion; the dilator tip including a proximal end, a distal end and a thickness in a direction substantially orthogonal to an axis between the proximal and distal ends of the dilator tip; wherein the dilator tip tapers for at least a part thereof in a direction from its proximal end to its distal end; and wherein the dilator tip for substantially all of said tapering part is oval in axial cross-section and increasingly flattens from the proximal end to the distal end over at least said portion; the dilator tip being more flexible in one radial orientation relative to another as a result of said oval cross-section.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

Figure 1:
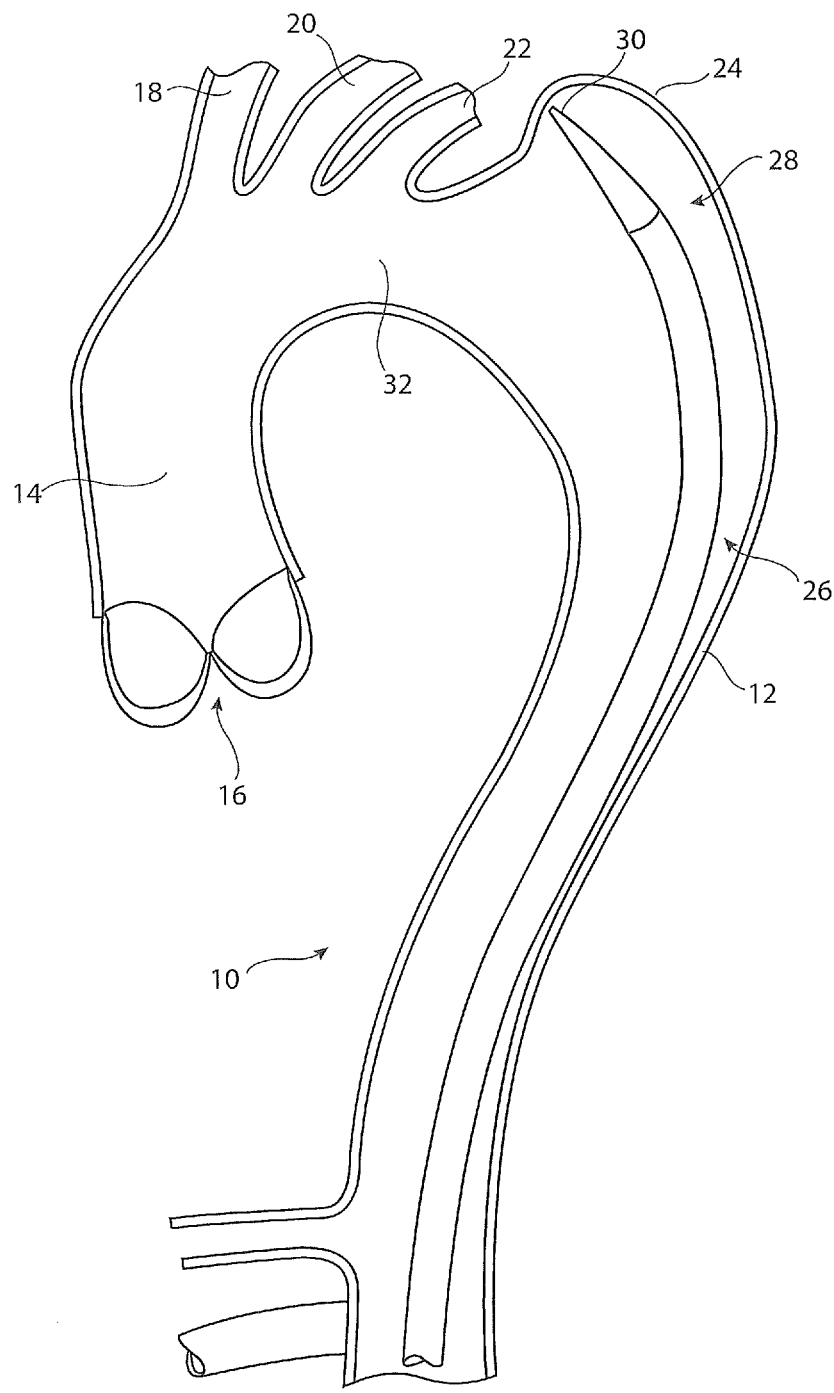
FIG. 1 shows in schematic form the aorta of a human which has an aneurysm; an introducer assembly having been inserted into the aorta.

Referring to FIG. 1, there is shown a cross-sectional view of a thoracic aorta 10 which includes descending aorta 12, ascending aorta 14, which receives blood from the heart through aortic valve 16. At the upper end of the ascending aorta there are the branches for the great vessels, the innominate artery 18, the left common carotid artery 20 and the left subclavian artery 22. The aorta after these great vessels is referred to as the descending aorta 12 and it is in this region that a thoracic aortic aneurysm 24 can occur. Aneurysms of this type must be treated as they can otherwise swell and burst with serious, often fatal, consequences. As shown in FIG. 1, an introducer or deployment assembly 26 has been deployed up through the descending aorta, typically over a guide wire (not shown in FIG. 1). The distal end 28 of the introducer assembly 26 is, in this example, located within the zone of the aneurysm 24. The distal end 28 is provided with a dilator tip 30, in this example of conventional construction. Given the tendency for the introducer assembly 26 to remain straight, it is possible, as shown in FIG. 1, for the distal end 28 of the introducer assembly and in particular the distal end of the dilator tip 30, to become caught in the aneurysm 24, in such a manner that the dilator tip 30 becomes stuck within the aneurysm 24 and is unable to move past this to guide the distal end 28 of the introducer assembly 26 around the aortic arch 32 towards the ascending aorta 14.

According to the teachings herein, there is provided a dilator tip with a non-round cross-section and in particular which has a smaller thickness in one angular direction relative to the other. In the preferred embodiments this could be described as being flattened, such as oval. As explained below, such a dilator tip assists in providing an introducer assembly which is able to negotiate past aneurysms such as the aneurysm 24. It is also explained below that the preferred embodiments of dilator tip are able to self-orient so as to orient the distal end 28 of the introducer assembly 26, thereby to orient a medical device or tool carried by the introducer assembly 26.

Figure 2:
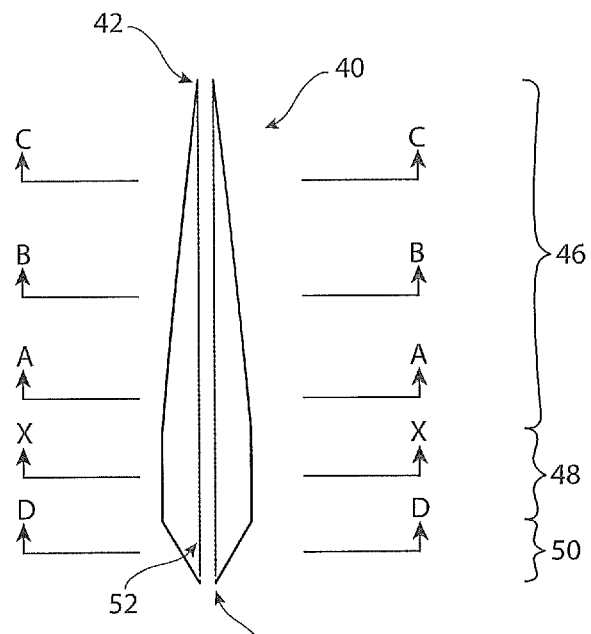
FIG. 2 is a schematic view of an embodiment of dilator tip for an introducer assembly.

With reference to FIG. 2, there is shown in general terms the form of the preferred embodiments of dilator tip 40. The tip 40 has a distal end 42, which typically constitutes the distal-most part of the introducer assembly 26, and a proximal end 44, which it typically fixed to a carrier catheter (not shown in FIG. 2). A bore 52 extends along the central longitudinal axis of the dilator tip 40, through which a guide wire (not shown in the Figure) of known form may pass.

In these embodiments, the dilator tip 40 has a tapering distal portion 46, which narrows towards the distal end 42, a generally cylindrical middle portion 48 and a short tapering proximal portion 50 which narrows towards the proximal end 44 of the dilator tip 40.

The proximal portion 44 is typically sized and shaped so as to fit into the distal end of a sheath of the introducer assembly, the wider end of the proximal portion 50 and the cylindrical portion 48 typically being wider than the internal diameter of the sheath to ensure that the dilator tip 40 cannot be slid entirely into the sheath.

The dilator tip is typically made of a compliant or elastomeric material including plastics and a rubber or rubber like materials. It will typically have a length in the region of a few centimeters in the case of a tip used for an aortic introducer, for instance 5 centimeters or so. Dilators for other applications will have other lengths.

Figure 3:
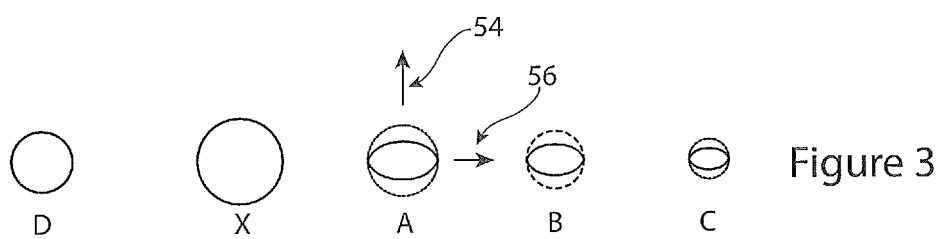
FIG. 3 shows various axial cross-sections of a first embodiment of dilator tip.
Figure 4:
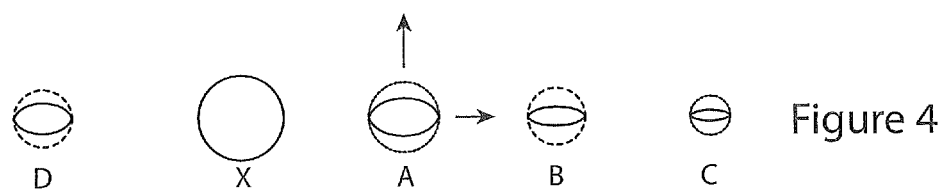
FIG. 4 shows various axial cross-sectional views of a second embodiment of dilator tip.
Figure 5:
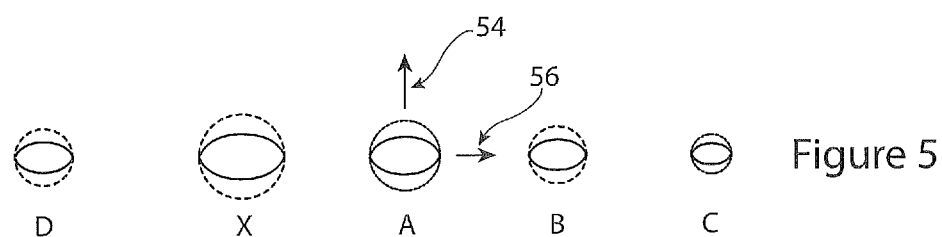
FIG. 5 shows various axial cross-sectional views of a third embodiment of dilator tip.

FIGS. 3 to 5 show a number of different embodiments of dilator tip, although it is to be understood that many other embodiments can be devised within the teachings herein and the scope of the claims. The embodiments of FIGS. 3 to 5 show various cross-sectional views of the tip 40 taken along lines D, X and A to C of FIG. 2.

Referring first to FIG. 3, as can be seen, portions 48 and 50 are generally round in axial cross-section (this being orthogonal or transverse to the longitudinal axis of the dilator tip 40 when straight). It will be appreciated that the proximal portion 50 becomes progressively narrower towards the proximal end 44, which in this embodiment retains its round form throughout its length.

On the other hand, the tapering distal portion 46 is non-round in axial cross-section as can be seen from the cross-sectional views A to C. In FIGS. 3A, 3B and 3C the dotted lines represent an imaginary circle so as to show the flattened, in this example oval, form of the dilator tip along portion 46. The oval form of this portion 46 of the dilator tip 40 causes the dilator tip to have a smaller thickness in one direction (direction 54 in FIG. 3) and a greater thickness in a second direction (direction 56 in FIG. 3). In this embodiment, with an oval or otherwise flattened dilator tip 40, the directions 54 and 56 are substantially orthogonal to one another.

In an embodiment, the ratio of widths in the two directions 54 and 56 remains substantially constant along the length of the distal portion 46.

The middle portion 48 of the dilator tip has a circular cylindrical shape, that is has an even diameter throughout its length, as shown by the cross-sectional view X of FIG. 3.

Referring now to FIG. 4, in this embodiment, the proximal portion 50 is also non-round, specifically being flattened or oval in axial cross-section. The intermediate portion 48 is of circular cylindrical shape, as with the embodiment of FIG. 3. The tapering distal portion 46 of this embodiment is also non-round in axial cross-section, similar to that of FIG. 3 but differs in having an increasingly pronounced flattening in a direction towards the distal end 42 of the dilator tip 40. In other words, the ratio of thicknesses in the directions 56:54 increases along the taper of the dilator tip portion 46. This results in the dilator tip 40 having an increasing flatness and thus a more pronounced radial difference in flexibilities along the length of the tip. It is to be appreciated that FIGS. 3 and 4 are just examples and that the features of these embodiments can be swapped from one embodiment to the other.

Referring now to FIG. 5, this shows an example of dilator tip 40 which has a flattened, preferably oval, configuration along the entirety of its length, that is over the distal tapering portion 46, the intermediate cylindrical portion 48 and the proximal tapering portion 50. This arrangement is can be particularly advantageous with dilator tips 40 which are provided with a relatively long cylindrical intermediate section 48 (much longer than the example shown in FIG. 2) and thus an intermediate portion 48 which is able to flex radially, particularly in direction 54. The example of FIG. 4 could have a flattening ratio (that is a ratio of thicknesses in directions 56:54) which is substantially constant along the length of the dilator tip 40 but in other embodiments could have different ratios of flattening along its length. The ratio of flattening could, for instance, be chosen so as to give the dilator tip 40 a substantially even flexibility in bending along the entirety of its length.

Figure 6:
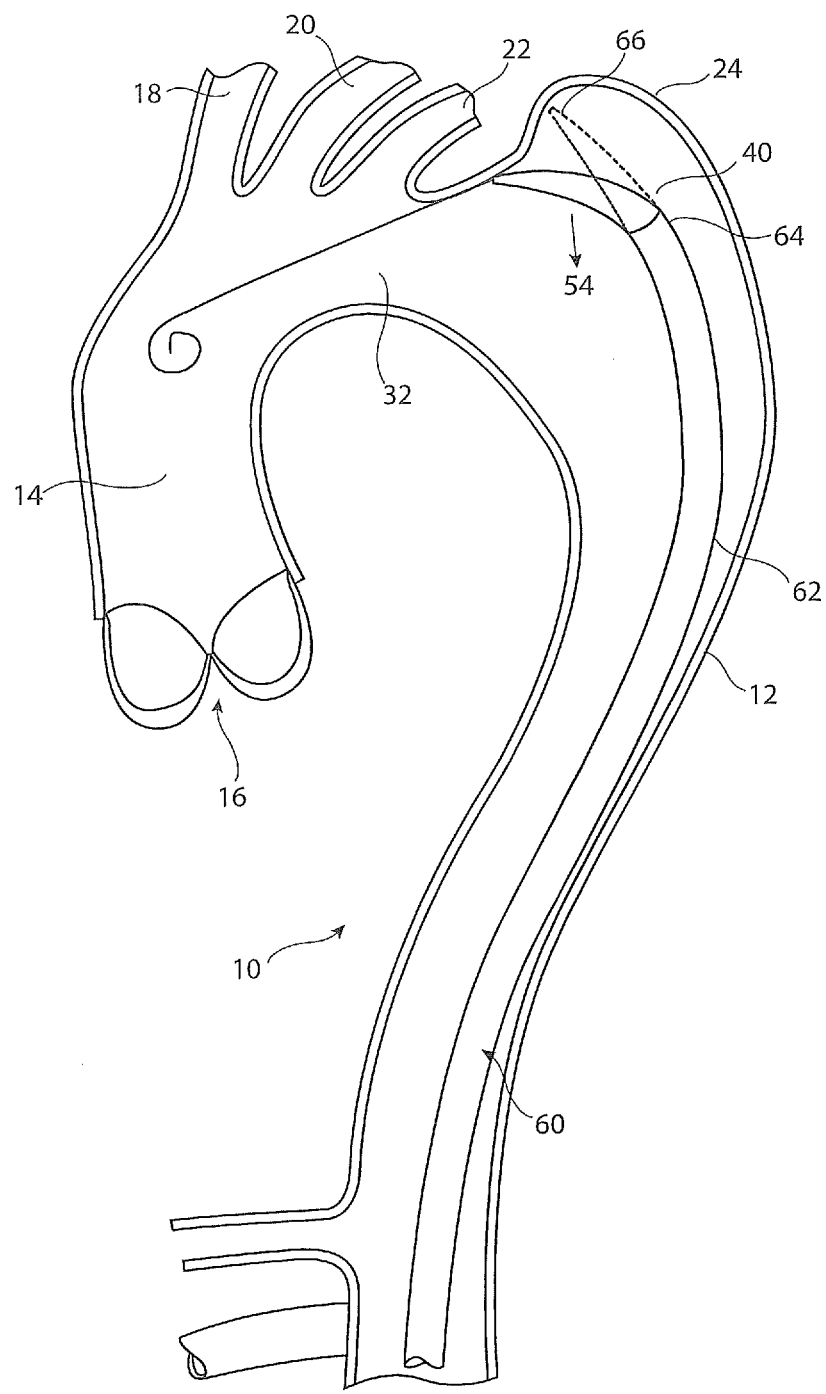
FIG. 6 is a schematic diagram of the aorta of a human patient showing the preferred embodiments of introducer assembly and dilator tip in use.

The flattened configuration of the dilator tip, it has been found, can substantially improve the trackability of the introducer and in particular the dilator tip 40 through tortuous vessels. Referring, for example, to FIG. 6, this is a view similar to FIG. 1 but of an introducer 60 which is provided with a dilator tip 40 as taught herein. The introducer 60 includes a sheath 62 which in some embodiments of entirely conventional construction and shape. In particular, the distal end 64 of the sheath 62 is shaped so as to confirm to the proximal portion 50 of the dilator tip 40 such that the proximal portion 50 connects within the distal end 64 of the sheath 62. In particular, the distal end 64 of the sheath 32 may have a shape to its internal wall which corresponds to the shape in axial cross-section of the proximal portion 50 of the dilator tip 40. Thus, for the embodiments of FIGS. 3 and 4, the luminal wall of sheath 62 at the distal end 64 is round, whereas it is oval for the embodiment of dilator tip of FIG. 5. The sheath 62 could have a uniform internal wall for the entirety or substantially the entirety of its length or could be so shaped only at it distal end 64.

The other components of the introducer assembly 60 can be of conventional form and include catheters, pusher elements, guide wire lumens, carrier elements for medical devices and so on. Such devices are well known in the art and thus not disclosed in here in any particular detail.

The dilator tip 40, as can be seen in FIG. 6, will exhibit different flexibilities in bending in dependence upon the radial orientation of the dilator tip 40, in accordance with the directions 54, 56 depicted in FIGS. 3 to 5. In the particular example of FIG. 6, the dilator tip 40 can be rotated (by rotation of the proximal/external end of the introducer assembly 60) so as to place one of the flattened sides against the wall of the aortic arch 32, in effect such that direction 54 is as shown by the arrow 54 in FIG. 6. The greater flexibility of the dilator tip 40 in this radial orientation can ensure that the dilator tip curves around the aneurysm 24, thereby facilitating the movement of the introducer 60 beyond the aneurysm 24, for the placement of, for example, a stent graft across the aneurysm. The dotted outline 66 shown in FIG. 6 represents what can happen with dilator tips of prior art designs and in particular which do not have enhanced or differing flexibilities in different radial directions.

The characteristics of the dilator tip 40, in particular the improved trackability, do not result solely from greater flexibility of the dilator tip but from the asymmetric flexibility in different radial directions. This enables the user, in effect, to alter the flexibility of the dilator tip 40 by rotating this, which can assist in guiding the dilator tip along tortuous vessels and in particular past obstructions such as aneurysm walls.

Figure 7:
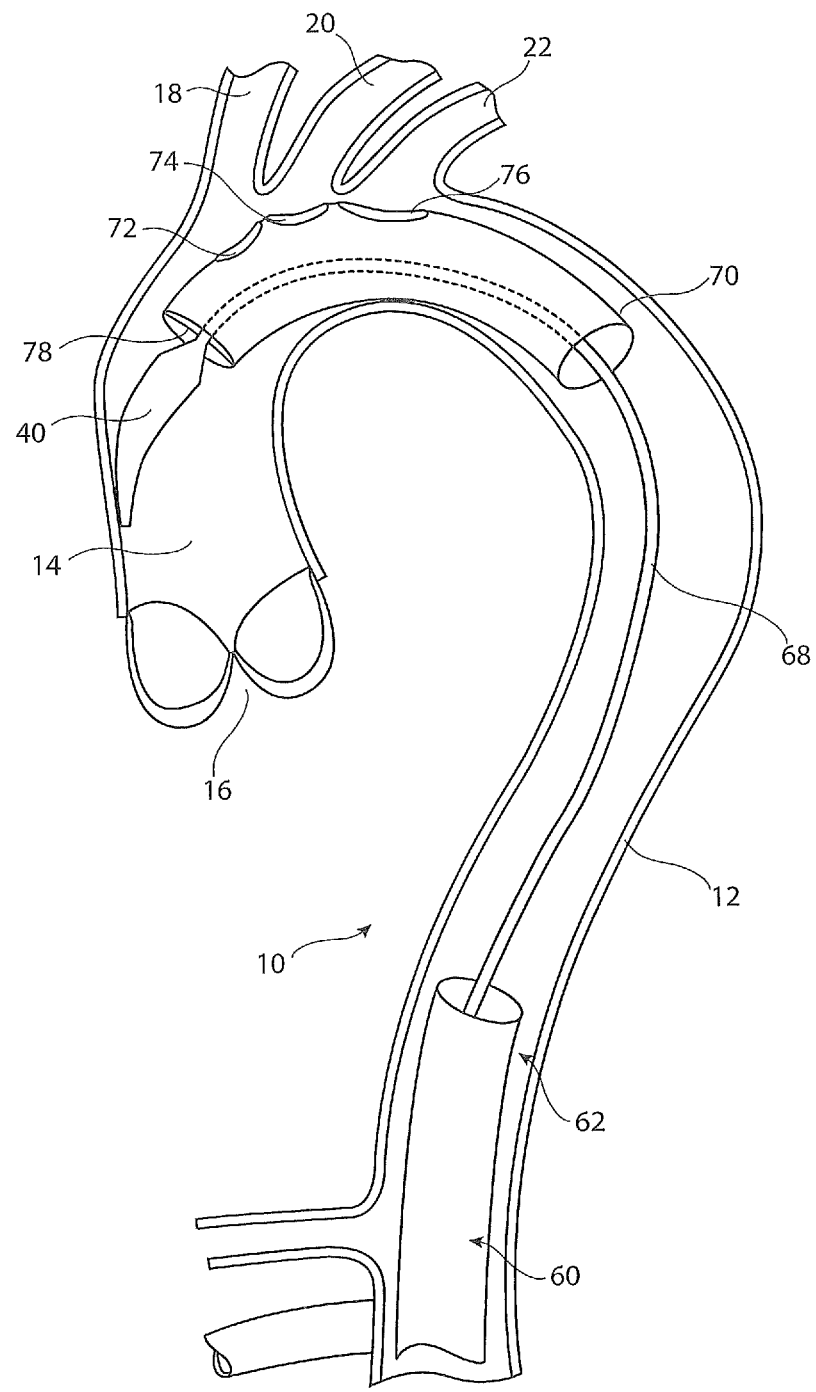
FIG. 7 is a schematic diagram showing use of the preferred embodiment of introducer assembly and dilator tip for the deployment of, in this example, a fenestrated stent graft.

FIG. 7 shows another example of operation which can be performed with advantage with dilator tip 40. FIG. 7 shows an introducer 60 used for the deployment of a fenestrated stent graft 70. For this purpose the introducer assembly 60 includes a carrier element 68 which is coupled to the dilator tip 40. The carrier element 68 can be of conventional form and include pusher rods and other components for use in holding a stent graft in the introducer during the deployment procedure and for the deployment operation. These components are well known in the art and therefore are not described in detail herein.

The dilator tip 40 will, as a result of its asymmetric or flattened shape, tend to rotate to one of two orientations (these orientations being equivalent to arrow 54 in FIGS. 3 to 5 and 180° to this) and not into the orthogonal direction 56. In other words, the dilator tip 40 will in practice self-orient to only one of two orientations. This can provide significant advantages in the deployment of medical devices or medical treatment tools which are rotationally dependent, for instance for fenestrated, branching or bifurcated stent grafts or other medical devices. It can also be useful for treatment tools which must be used in a particular orientation.

In the example shown in FIG. 7, stent graft 70 is provided with three fenestrations 72, 74 and 76 which during the deployment operation need to be aligned, respectively, with the brachiocephalic artery 18, the left common carotid artery 20 and the left subclavian artery 22. For this purpose, the stent graft 70 is attached by a suitable restraining device 78, to the introducer 60 in a specific orientation relative to the orientation of the dilator tip 40, such that when in the curved configuration shown in FIG. 7, the self-orienting nature of the dilator tip 40 will automatically orient the fenestrations 72-76 in substantial alignment with the arteries 18-22. It will be appreciated that the dilator tip 40 may in some circumstances be deployed so as to be oriented 180° to the configuration shown in FIG. 7, in which case rotation of the introducer assembly 60 at its proximal/external end, can be effected so as to cause the dilator tip 40 to "flip" to its opposite orientation and therefore such that the fenestrations 72-76 are properly oriented with respect to the arteries 18-22. Such a flipping operation is relatively easy given the fact that the dilator tip 40 will tend to self-orient, with the result that rotation of the introducer assembly does not have to be carried out in a very precise manner, as is necessary, for instance, with existing introducer assemblies.

The introducer assembly and/or medical device 70 could usefully be provided with radiopaque markers to indicate the rotational orientation of the distal end 28 of the assembly. Markers of this type are well known in the art and therefore not described in detail herein.

Although the preferred embodiments of dilator tip disclosed herein have a tapering distal portion, this is not necessary. The distal portion 46 of the dilator tip 40 could for instance be cylindrical. The flattened nature of the dilator tip 40 can in at least some implementations provide the dilator tip with the required flexibility even when this is generally cylindrical.

Similarly, it is not necessary for the whole of the distal tip portion 46 of the dilator tip 40 to be flattened, that is for the asymmetric shape to extend all the way to the distal end 42 of the dilator tip 40. The distal end 42 could, in some implementations, be rounded in cross-section with the asymmetric or flattened portion being located proximally of this, for instance to extend only over an intermediate portion of the dilator tip 40. One example could have a circular tip 42, a non-round intermediate portion 46, and circular portions 48 and 50. Other examples could have any of the other configurations shown and described, for instance, in FIGS. 4 and 5.

The invention claimed is:

1. An introducer assembly for the deployment of medical devices within a lumen of a patient;
    the assembly including a sheath member provided with at least one lumen therein for housing an implantable medical device or medical treatment apparatus, and a dilator tip extending beyond a distal extremity of the sheath member;
    the dilator tip including a proximal part, a bore, proximal end, a distal end, and a thickness in a direction orthogonal to an axis between the proximal and distal ends;
    wherein the dilator tip is, for at least a portion of its extent between the proximal and distal ends, flattened so as to be less in one angular direction relative to another as measured along an axial cross section orthogonal to the axis between the proximal and distal ends; and
    wherein the distal end of the dilator tip is flattened;
    the dilator tip being more flexible in one radial orientation relative to another as a result of said flattening;
    the bore extending through the distal end; and
    the proximal part becoming progressively narrower towards the proximal end and not tapered in a direction towards the distal end of the dilator tip; and
    wherein said proximal part is non-round in axial cross-section.

2. An introducer assembly according to claim 1, wherein the dilator tip is oval in cross-section in said orthogonal direction for at least said portion.

3. An introducer assembly according to claim 1, wherein the dilator tip tapers for at least a part thereof in a direction from its proximal end to its distal end.

4. An introducer assembly according to claim 3, wherein the said portion extends along substantially the entirety of the tapering part of the dilator tip.

5. An introducer assembly according to claim 1, wherein the dilator tip is varyingly flattened over at least said portion.

6. An introducer assembly according to claim 5, wherein the dilator tip is increasingly flattened in a direction from its distal end to its proximal end.

7. An introducer assembly according to claim 6, wherein said increasing flattening is gradual over at least said portion.

8. An introducer assembly according to claim 1, wherein said dilator tip is formed from an elastomeric material, a plastics material, or a rubber or rubber like material.

9. An introducer assembly according to claim 1, wherein the dilator tip includes a central lumen for the passage of a guide wire therethrough.

10. An introducer assembly according to claim 1, wherein the introducer assembly includes fixings for fixing an implantable medical device or other medical element in the introducer in a specific radial orientation, which radial orientation is aligned with the radial orientation of the dilator tip.

11. An introducer assembly according to claim 1, including an implantable medical device or other medical element having a given radial orientation profile, which profile is aligned with the radial orientation of the dilator tip.

12. An introducer assembly according to claim 1, wherein a wider end of said proximal part is wider than the internal diameter of the sheath member.

13. An introducer assembly for the deployment of medical devices within a lumen of a patient;
    the assembly including a sheath member provided with at least one lumen therein for housing an implantable medical device or medical treatment apparatus, and a dilator tip extending beyond a distal extremity of the sheath member;
    the dilator tip including a proximal part, a bore, proximal end, a distal end, and a thickness in a direction orthogonal to an axis between the proximal and distal ends;
    wherein the dilator tip is, for at least a portion of its extent between the proximal and distal ends, flattened so as to be less in one angular direction relative to another as measured along an axial cross section orthogonal to the axis between the proximal and distal ends; and
    wherein the distal end of the dilator tip is flattened;
    the dilator tip being more flexible in one radial orientation relative to another as a result of said flattening;
    the bore extending through the distal end; and
    the proximal part becoming progressively narrower towards the proximal end and not tapered in a direction towards the distal end of the dilator tip; and
    wherein said proximal part is non-round in axial cross-section; and
    wherein said proximal part is substantially flattened in axial cross-section.

* * * * *